US008889923B2

(12) United States Patent  
Johnston et al.

(10) Patent No.: US 8,889,923 B2
(45) Date of Patent: *Nov. 18, 2014

(54) SYNTHESIS OF ETHANOL FROM BIOMASS

(75) Inventors: Victor J. Johnston, Houston, TX (US); Barbara F. Kimmich, Bernardsville, NJ (US); Jan Cornelis van der Waal, Delft (NL); James H. Zink, League City, TX (US); Virginie Zuzaniuk, Krommenie (NL); Josefina T. Chapman, Houston, TX (US); Laiyuan Chen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/215,829

(22) Filed: Aug. 23, 2011

(65) Prior Publication Data

US 2011/0306806 A1 Dec. 15, 2011

Related U.S. Application Data

(63) Continuation of application No. 13/056,470, filed as application No. PCT/US2009/004197 on Jul. 20, 2009, which is a continuation of application No. 12/221,239, filed on Jul. 31, 2008, now Pat. No. 7,608,744.

(51) Int. Cl.
*C07C 29/149* (2006.01)
*C07C 29/147* (2006.01)

(52) U.S. Cl.
CPC .......... *C07C 29/147* (2013.01); *C07C 29/149* (2013.01); *Y02E 50/32* (2013.01)
USPC ........................................................ 568/885

(58) Field of Classification Search
USPC ........................................................ 568/885
See application file for complete search history.

(56) References Cited

U.S. PATENT DOCUMENTS

| | | | |
|---|---|---|---|
| 2,607,807 A | 8/1952 | Ford | |
| 2,744,939 A | 5/1956 | Kennel | |
| 3,478,112 A | 11/1969 | Adam et al. | |
| 3,990,952 A | 11/1976 | Katzen et al. | |
| 4,317,918 A | 3/1982 | Takano et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,443,639 A | 4/1984 | Pesa et al. | |
| 4,480,115 A | 10/1984 | McGinnis | |
| 4,517,391 A | 5/1985 | Schuster et al. | |
| 4,550,185 A | 10/1985 | Mabry et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,985,572 A | 1/1991 | Kitson et al. | |
| 4,990,655 A | 2/1991 | Kitson et al. | |
| 5,008,235 A | 4/1991 | Wegman et al. | |
| 5,061,671 A | 10/1991 | Kitson et al. | |
| 5,124,004 A | 6/1992 | Grethlien et al. | |
| 5,137,861 A | 8/1992 | Shih et al. | |
| 5,149,680 A | 9/1992 | Kitson et al. | |
| 5,155,084 A | 10/1992 | Horn et al. | |
| 5,243,095 A | 9/1993 | Roberts et al. | |
| 5,350,504 A | 9/1994 | Dessau | |
| RE35,377 E | 11/1996 | Steinberg et al. | |
| 5,821,111 A | 10/1998 | Grady et al. | |
| 5,945,570 A | 8/1999 | Arhancet et al. | |
| 6,049,008 A | 4/2000 | Roberts et al. | |
| 6,232,352 B1 | 5/2001 | Vidalin et al. | |
| 6,294,703 B1 | 9/2001 | Hara et al. | |
| 6,462,231 B1 | 10/2002 | Yanagawa et al. | |
| 6,495,730 B1 | 12/2002 | Konishi et al. | |
| 6,509,180 B1 | 1/2003 | Verser et al. | |
| 6,632,330 B1 | 10/2003 | Colley et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,906,228 B2 | 6/2005 | Fischer et al. | |
| 6,927,048 B2 | 8/2005 | Verser et al. | |
| 7,297,236 B1 | 11/2007 | Vander Griend | |
| 7,425,657 B1 | 9/2008 | Elliott et al. | |
| 7,507,562 B2 | 3/2009 | Verser et al. | |
| 7,538,060 B2 | 5/2009 | Barnicki et al. | |
| 7,553,397 B1 | 6/2009 | Colley et al. | |

(Continued)

FOREIGN PATENT DOCUMENTS

| | | | |
|---|---|---|---|
| EP | 0137749 A2 | 4/1985 | |
| EP | 0167300 A1 | 1/1986 | |
| EP | 0104197 | 5/1986 | |
| EP | 0285420 | 10/1988 | |
| EP | 0285420 B1 | 10/1988 | |
| EP | 0372847 | 6/1990 | |
| EP | 0372847 A2 | 6/1990 | |
| EP | 0990638 | 4/2000 | |
| EP | 0990638 A1 | 4/2000 | |
| EP | 1262234 | 12/2002 | |

(Continued)

OTHER PUBLICATIONS

Acala, et al., (2005). Experimental and EFT studies of the conversion of ethanol and acetic acid on PtSn-based catalysts, Journal of Physical Chemistry, 109(6), 2074-2085.

(Continued)

*Primary Examiner* — Elvis O Price

(57) ABSTRACT

A process for the selective production of ethanol by vapor phase reaction of acetic acid over a hydrogenating catalyst composition to form ethanol is disclosed and claimed. In an embodiment of this invention reaction of acetic acid and hydrogen over either cobalt and palladium supported on graphite or cobalt and platinum supported on silica selectively produces ethanol in a vapor phase at a temperature of about 250° C.

32 Claims, No Drawings

(56) References Cited

U.S. PATENT DOCUMENTS

| | | |
|---|---|---|
| 7,572,353 B1 | 8/2009 | van der Griend |
| 7,608,744 B1 | 10/2009 | Johnston et al. |
| 7,863,489 B2 | 1/2011 | Johnston et al. |
| 7,884,253 B2 | 2/2011 | Stites et al. |
| 2003/0077771 A1 | 4/2003 | Verser et al. |
| 2003/0104587 A1 | 6/2003 | Verser |
| 2004/0195084 A1 | 10/2004 | Hetherington et al. |
| 2006/0019360 A1 | 1/2006 | Verser et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2009/0023192 A1 | 1/2009 | Verser et al. |
| 2009/0166172 A1 | 7/2009 | Casey |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029996 A1 | 2/2010 | Danjo et al. |
| 2010/0121114 A1 | 5/2010 | Weiner et al. |

FOREIGN PATENT DOCUMENTS

| | | |
|---|---|---|
| EP | 1262234 A2 | 12/2002 |
| EP | 1277826 A1 | 1/2003 |
| EP | 2186787 | 5/2010 |
| GB | 1168785 | 10/1969 |
| GB | 1559540 | 1/1980 |
| GB | 2136704 | 9/1987 |
| JP | 6-116182 | 4/1994 |
| JP | 10-306047 A | 11/1998 |
| JP | 11-147845 | 6/1999 |
| JP | 2001-046874 A | 2/2001 |
| JP | 2001-157841 A | 6/2001 |
| WO | WO 83/03409 A1 | 10/1983 |
| WO | WO 2003/097523 A2 | 11/2003 |
| WO | WO 2004/101488 A1 | 11/2004 |
| WO | WO 2005/102513 | 11/2005 |
| WO | WO 2009/063176 | 5/2009 |
| WO | WO 2009/086839 | 7/2009 |
| WO | WO 2009/105860 A1 | 9/2009 |
| WO | WO 2010/055285 A1 | 5/2010 |

OTHER PUBLICATIONS

Amit M. Goda et al., DFT modeling of selective reduction of acetic acid to acetaldehyde on Pt-based bimetallic catalysts, $20_{th}$ NAM, Houston, TX, Jun. 17-22, 2007, available online at <http://www.nacatsoc.org/20nam/abstracts/O-S9-18.pdf>.

Brunauer, Emmett and Teller J, Am. Chem. Soc. 60, 309 (1938); and Proc. Roy Soc. A314, pp. 473-498.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Ordonez et al., The role of metal and support sites on the hydrogenation of acetic acid on Ru-based catalysts, $21_{st}$ NAM San Francisco, CA, Jun. 10, 2009.

Pallassana et al., Reaction Paths in the Hydrogenolysis of Acetic Acid to Ethanol over Pd(111), Re(0001), and PdRe Alloys, Journal of Catalysis 209:289-305 (2002).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Proc. Roy Soc. A314, pp. 473-498 (1970).

Rachmady, Acetic Acid Reduction by H2 on Bimetallic Pt-Fe Catalysts, Journal of Catalysis 209, 87-98 (Apr. 1, 2002), Elsevier Science (USA).

Santori et al., (2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-derived syngas", Chemical Society Reviews, 2007, 36, pp. 1514-1528.

Subramani et al., "A Review of Recent Literature to Search for an Efficient Catalytic Process for the Conversion of Syngas to Ethanol", Energy and Fuels 2008, 22, pp. 814-839.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry. Applied Organometallic Chemistry, 21(10), 836-840.

Extended European Search Report for EP 11 17 9264 mailed Oct. 25, 2011 (5 Pages).

International Search Report and Written Opinion for PCT/US2009/004197 mailed Mar. 24, 2010 (14 Pages).

International Search Report and Written Opinion for PCT/US2009/004195 mailed Mar. 26, 2010 (12 pages).

International Preliminary Report on Patentability for PCT/US2009/004197 mailed Aug. 10, 2010 (9 Pages).

Non-final Office Action for U.S. Appl. No. 13/056,470 mailed Aug. 31, 2012.

Non-final Office Action for U.S. Appl. No. 13/079,679 mailed Sep. 14, 2012.

Office Action for corresponding Chinese Application No. 20098056622.0 dated Nov. 21, 2013.

SYNTHESIS OF ETHANOL FROM BIOMASS

CROSS-REFERENCE TO RELATED APPLICATIONS

This is a continuation of U.S. patent application Ser. No. 13/056,470, which is a national stage of PCT/US2009/004197, filed on Jul. 20, 2009, which claims priority to U.S. patent application Ser. No. 12/221,239, filed Jul. 31, 2008, now U.S. Pat. No. 7,608,744, each of which is incorporated herein by reference in its entirety.

FIELD OF THE INVENTION

The present invention relates generally to a process for the production of ethanol from acetic acid. More specifically, the present invention relates to a process including hydrogenating acetic acid utilizing a catalyst to form ethanol with high selectivity.

BACKGROUND

There is a long felt need for an economically viable process to convert acetic acid to ethanol. Ethanol is an important commodity feedstock for a variety of industrial products and is also used as a fuel additive with gasoline. Ethanol can readily be dehydrated to ethylene, which can then be converted to a variety of products, both polymeric and small molecule-based. Ethanol is conventionally produced from feedstocks where price fluctuations are becoming more significant. That is, fluctuating natural gas and crude oil prices contribute to fluctuations in the cost of conventionally produced, petroleum, natural gas or corn or other agricultural product-sourced ethanol, making the need for alternative sources of ethanol all the greater when oil prices and/or agricultural product prices rise.

It has been reported that ethanol can be produced from the hydrogenation of acetic acid, but most of these processes feature several drawbacks for a commercial operation. For instance, U.S. Pat. No. 2,607,807 discloses that ethanol can be formed from acetic acid over a ruthenium catalyst at extremely high pressures of 700-950 bars in order to achieve yields of around 88%, whereas low yields of only about 40% are obtained at pressures of about 200 bar. Nevertheless, both of these conditions are unacceptable and uneconomical for a commercial operation.

More recently, it has been reported that ethanol can be produced from hydrogenating acetic acid using a cobalt catalyst again at superatmospheric pressures such as about 40 to 120 bar. See, for example, U.S. Pat. No. 4,517,391 to Shuster al. However, the only example disclosed therein employs reaction pressure in the range of about 300 bar still making this process undesirable for a commercial operation. In addition, the process calls for a catalyst containing no less than 50 percent cobalt by weight plus one or more members selected from the group consisting of copper, manganese, molybdenum, chromium, and phosphoric acid, thus rendering the process economically non-viable. Although there is a disclosure of use of simple inert catalyst carriers to support the catalyst materials, there is no specific example of supported metal catalysts.

U.S. Pat. No. 5,149,680 to Kitson et al. describes a process for the catalytic hydrogenation of carboxylic acids and their anhydrides to alcohols and/or esters utilizing a platinum group metal alloy catalysts. The catalyst is comprised of an alloy of at least one noble metal of group VIII of the Periodic Table and at least one metal capable of alloying with the group VIII noble metal, admixed with a component comprising at least one of the metals rhenium, tungsten or molybdenum. Although it has been claimed therein that improved selectivity to alcohols are achieved over the prior art references it was still reported that 3 to 9 percent of alkanes, such as methane and ethane are formed as by-products during the hydrogenation of acetic acid to ethanol under their optimal catalyst conditions.

U.S. Pat. No. 4,777,303 to Kitson et al. describes a process for the productions of alcohols by the hydrogenation of carboxylic acids. The catalyst used in this case is a heterogeneous catalyst comprising a first component which is either molybdenum or tungsten and a second component which is a noble metal of Group VIII of the Periodic Table of the elements, optionally on a support, for example, a high surface area graphitized carbon. The selectivity to a combined mixture of alcohol and ester is reported to be only in the range of about 73 to 87 percent with low conversion of carboxylic acids at about 16 to 58 percent. In addition, no specific example of conversion of acetic acid to ethanol is provided.

U.S. Pat. No. 4,804,791 to Kitson et al. describes another process for the productions of alcohols by the hydrogenation of carboxylic acids. In this process, ethanol is produced from acetic acid or propanol is produced from propionic acid by contacting either acetic acid or propionic acid in the vapor phase with hydrogen at elevated temperature and a pressure in the range from 1 to 150 bar in the presence of a catalyst comprising as essential components (i) a noble metal of Group VIII of the Periodic Table of the elements, and (ii) rhenium, optionally on a support, for example a high surface area graphitized carbon. The conversion of acetic acid to ethanol ranged from 0.6% to 69% with selectivity to ethanol was in the range of about 6% to 97%.

From the foregoing it is apparent that existing processes do not have the requisite selectivity to ethanol or existing art employs catalysts, which are expensive and/or non selective for the formation of ethanol and produces undesirable by-products.

SUMMARY OF THE INVENTION

It has now been unexpectedly found that ethanol can be made on an industrial scale directly from acetic acid with high selectivity and yield. More particularly, this invention provides a process for the selective formation of ethanol from acetic acid comprising: hydrogenating acetic acid over a suitable hydrogenating catalyst in the presence of hydrogen. The catalyst suitable for the process of this invention is comprised of about 0.1 weight percent to about 20 weight percent of cobalt supported on a suitable catalyst support in combination with one or more metal catalysts selected from the group consisting of palladium, platinum, rhodium, ruthenium, rhenium, iridium, chromium, copper, tin, molybdenum, tungsten, vanadium and zinc. Suitable catalyst supports include without any limitation, silica, alumina, calcium silicate, silica-alumina, carbon, zirconia and titania.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Mole percent (mole % or %) and like terms refer to mole percent unless otherwise indicated. Weight percent (wt % or %) and like terms refer to weight percent unless otherwise indicated.

"Conversion" is expressed as a mole percentage based on acetic acid in the feed. The conversion of acetic acid (AcOH) is calculated from gas chromatography (GC) data using the following equation:

$$\text{AcOH conversion (\%)} = 100 * \frac{\text{mmol AcOH in (feed stream)} - \text{mmol AcOH out } (GC)}{\text{mmol AcOH in (feed stream)}}$$

"Selectivity" is expressed as a mole percent based on converted acetic acid. For example, if the conversion is 50 mole % and 50 mole % of the converted acetic acid is converted to ethanol, we refer to the ethanol selectivity as 50%. Selectivity to ethanol (EtOH) is calculated from gas chromatography (GC) data using the following equation:

$$\text{Selectivity to EtOH (\%)} = 100 * \frac{\text{mmol EtOH out } (GC)}{\frac{\text{Total mmol C out } (GC)}{2} - \text{mmol AcOH out } (GC)}$$

Weight percent of a catalyst metal is based on metal weight and the total dry weight of metal and support.

The reaction proceeds in accordance with the following chemical equation:

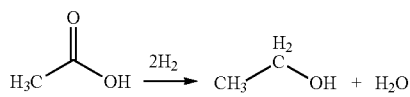

In accordance with the invention, conversion of acetic acid to ethanol can be carried out in a variety of configurations, such as for example in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce ethanol. Any suitable particle size may be used depending upon the type of reactor, throughput requirements and so forth.

Although various hydrogenating catalysts known to one skilled in the art can be employed in hydrogenating acetic acid to form ethanol in the process of this invention it is preferred that a hydrogenating catalyst employed contains about 0.1 weight percent to about 20 weight percent of cobalt on a suitable catalyst support. As noted earlier, it is further preferred that the catalysts that are suitable in the process of this invention contain optionally a second and/or a third metal supported on the same catalyst support. The following metals may be mentioned as those metals suitable as a second and/or third metals without any limitation: palladium, platinum, rhodium, ruthenium, rhenium, iridium, chromium, copper, tin, molybdenum, tungsten, vanadium, zinc and a mixture thereof. Typically, it is preferred that cobalt in combination with at least one other metal on a suitable support can be used as a hydrogenating catalyst. Thus cobalt in combination with either palladium or platinum are particularly preferred. Similarly, cobalt in combination with ruthenium, chromium or vanadium is also preferred. Examples of metals that can be used with cobalt as a third metal include without any limitation any of the other metals listed above, such as for example rhodium, iridium, copper, tin molybdenum and zinc.

Various catalyst supports known in the art can be used to support the catalysts of this invention. Examples of such supports include without any limitation, zeolite, iron oxide, silica, alumina, titania, zirconia, silica-alumina, magnesium oxide, calcium silicate, carbon, graphite and a mixture thereof. Preferred supports are silica, alumina, calcium silicate, carbon, zirconia and titania. More preferably silica is used as a catalyst support in the process of this invention. It is also important to note that higher the purity of silica better it is preferred as a support in this invention. Another preferred catalyst support is calcium silicate.

In another embodiment of this invention the preferred catalyst support is carbon. Various forms of carbon known in the art that are suitable as catalyst support can be used in the process of this invention. Particularly preferred carbon support is a graphitized carbon, particularly the high surface area graphitized carbon as described in Great Britain Patent No. 2,136,704. The carbon is preferably in particulate form, for example, as pellets. The size of the carbon particles will depend on the pressure drop acceptable in any given reactor (which gives a minimum pellet size) and reactant diffusion constraint within the pellet (which gives a maximum pellet size).

The carbon catalyst supports that are suitable in the process of this invention preferably porous carbon catalyst supports. With the preferred particle sizes the carbon will need to be porous to meet the preferred surface area characteristics.

The catalyst supports including the carbon catalyst supports may be characterized by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473-498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred carbon catalyst supports for use in the present invention have a BET surface area of at least 100 m$^2$/g, more preferably at least 200 m$^2$/g, most preferably at least 300 m$^2$/g. The BET surface area is preferably not greater than 1000 m$^2$/g, more preferably not greater than 750 m$^2$/g.

The preferred carbon support may be prepared by heat treating a carbon-containing starting material. The starting material may be an oleophillic graphite e.g. prepared as disclosed in Great Britain Patent No. 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than these indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidizing agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidizing agents are steam, carbon dioxide, and gases containing molecular oxygen e.g. air. The oxidation is preferably carried out to give a carbon weight loss of at least 10 weight percent based on weight of carbon subjected to the oxidation step, more preferably at least 15 weight percent.

The weight loss is preferably not greater than 40 weight percent of the carbon subjected to the oxidation step, more preferably not greater than 25 weight percent of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

As noted above, the loading levels of cobalt on the catalyst support is generally in the range of about 0.1 weight percent to about 20 weight percent. The amount of second or third metal loading on a support is not very critical in this invention and can vary in the range of about 0.1 weight percent to about 10 weight percent. A metal loading of about 1 weight percent to about 6 weight percent based on the weight of the support is particularly preferred. Thus, for example 0.5 to 2 weight percent of palladium supported on graphite which contains about 4 to 12 weight percent of cobalt is particularly a preferred catalyst. Similarly, a catalyst containing about 0.5 to 2 weight percent of platinum supported on high purity silica which contains about 4 to 12 weight percent of cobalt is also a preferred catalyst.

As already noted above, other metals that can preferably be used as second metal with cobalt include ruthenium, chromium and vanadium. In each of these cases cobalt loading of 4 to 12 weight percent with second metal, i.e., ruthenium, chromium or vanadium loading of about 0.5 to 2 weight percent are preferred. If a third metal is employed, its loading can also be in the range of about 0.5 weight percent to about 2 weight percent, however, higher levels of metal loadings can also be used depending upon the type of metal and the catalyst support used.

The metal impregnation can be carried out using any of the known methods in the art. Typically, before impregnation the supports are dried at 120° C. and shaped to particles having size distribution in the range of about 0.2 to 0.4 mm. Optionally the supports may be pressed, crushed and sieved to a desired size distribution. Any of the known methods to shape the support materials into desired size distribution can be employed.

For supports having low surface area, such as for example alpha-alumina, the metal solutions are added in excess until complete wetness or excess liquid impregnation so as to obtain desirable metal loadings.

As noted above, the hydrogenation catalysts used in the process of this invention are at least bimetallic having cobalt as the main metal. Generally, without intending to be bound by any theory, it is believed that one metal acts as a promoter metal and the other metal is the main metal. For instance, in the instant process of the invention, cobalt is considered to be main metal for preparing hydrogenation catalysts of this invention. The main metal can be combined with a promoter metal such as tungsten, vanadium, molybdenum, chromium or zinc. However, it should be noted that sometimes main metal can also act as a promoter metal or vice versa. For example, nickel can be used as a promoter metal when iron is used as a main metal. Similarly, chromium can be used as a main metal in conjunction with copper (i.e., Cu—Cr as main bimetallic metals), which can further be combined with promoter metals such as cerium, magnesium or zinc.

The bimetallic catalysts are generally impregnated in two steps. First, the "promoter" metal is added, followed by "main" metal. Each impregnation step is followed by drying and calcination. The bimetallic catalysts may also be prepared by co-impregnation. In the case of trimetallic Cu/Cr-containing catalysts as described above, a sequential impregnation may be used, starting with the addition of the "promoter" metal. The second impregnation step may involve co-impregnation of the two principal metals, i.e., Cu and Cr. For example, Cu—Cr—Co on SiO$_2$ may be prepared by a first impregnation of chromium nitrate, followed by the co-impregnation of copper and cobalt nitrates. Again, each impregnation is followed by drying and calcinations. In most cases, the impregnation may be carried out using metal nitrate solutions. However, various other soluble salts which upon calcination releases metal ions can also be used. Examples of other suitable metal salts for impregnation include metal hydroxide, metal oxide, metal acetate, ammonium metal oxide, such as ammonium heptamolybdate hexahydrate, metal acids, such as perrhenic acid solution, metal oxalate, and the like.

Thus in one embodiment of this invention, there is provided a hydrogenation catalyst wherein the catalyst support is graphite with a bimetallic loading of cobalt and palladium. In this aspect of the invention, the loading of cobalt is about ten (10) weight percent and the loading of palladium is about one (1) weight percent. A loading level of cobalt at five (5) weight percent and loading level of palladium at 0.5 weight percent can also be employed if so desired.

In another embodiment of this invention, there is further provided a hydrogenation catalyst wherein the catalyst support is high purity silica with a bimetallic loading of cobalt and platinum. In this aspect of the invention, the loading of cobalt is about ten (10) weight percent and the loading of platinum is about one (1) weight percent. Again in this aspect of the invention, loading levels of cobalt at five (5) weight percent and loading levels of platinum at 0.5 weight percent can also be employed.

In general, by the practice of this invention acetic acid can selectivity be converted to ethanol at very high rates. The selectivity to ethanol in general is very high and may be at least 40 percent. Under preferred reaction conditions, acetic acid is selectively converted to ethanol at a selectivity of about 60 percent or more preferably at a selectivity of at least 80 percent. Most preferably ethanol selectivity is at least 95 percent.

In another aspect of the process of this invention, the hydrogenation is carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 200° C. to about 300° C., preferably about 225° C. to about 275° C. The pressure is generally uncritical to the reaction and subatmospheric, atmospheric or superatmospheric pressures may be employed. In most cases, however, the pressure of the reaction will be in the range of about 1 to 30 atmospheres absolute, most preferably the pressure of reaction zone is in the range of about 10 to 25 atmospheres absolute.

Although the reaction consumes two moles of hydrogen per mole of acetic acid to produce a mole of ethanol, the actual molar ratio of acetic acid to hydrogen in the feed stream may be varied between wide limits, e.g. from about 100:1 to 1:100. It is preferred however that such ratio be in the range of about 1:20 to 1:2. More preferably the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 Grady et al., which discloses a process for converting waste biomass through gasification into synthesis gas as well as U.S. Pat. No. 6,685,754 Kindig et al., the disclosures of which are incorporated herein by reference.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 of Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

In one of the preferred embodiments there is also provided a process for selective and direct formation of ethanol from acetic acid comprising: contacting a feed stream containing acetic acid and hydrogen at an elevated temperature with a suitable hydrogenating catalyst containing about 1 weight percent to about 15 weight percent of cobalt on a suitable catalyst support and a second metal supported on said support and wherein said second metal is selected from the group consisting of palladium, platinum, copper, tin, molybdenum and tungsten.

In this embodiment of the process of this invention, the preferred hydrogenation catalyst contains one (1) weight percent palladium or platinum with about ten (10) weight percent cobalt. In this embodiment of the process of this invention it is preferred that the hydrogenation catalysts is layered in a fixed bed and the reaction is carried out in the vapor phase using a feed stream of acetic acid and hydrogen in the molar range of about 1:20 to 1:2 and at a temperature in the range of about 225° C. to 275° C. and at a pressure of reaction zones in the range of about 10 to 25 atmospheres absolute, and the contact time of reactants is in the range of about 0.5 and 100 seconds.

The following examples describe the procedures used for the preparation of various catalysts employed in the process of this invention.

EXAMPLE A

Preparation of 10 Weight Percent cobalt and 1 Weight Percent Palladium on Graphite Powdered and meshed graphite (100 g) of uniform particle size distribution of about 0.2 mm was dried at 120° C. in an oven under nitrogen atmosphere overnight and then cooled to room temperature. To this was added a solution of palladium nitrate (Heraeus) (2.2 g) in distilled water (22 ml). The resulting slurry was dried in an oven gradually heated to 110° C. (>2 hours, 10° C./min.). The impregnated catalyst mixture was then calcined at 500° C. (6 hours, 1° C./min). To this calcined and cooled material was added a solution of cobalt nitrate hexahydrate (49.4 g) in distilled water (50 ml). The resulting slurry was dried in an oven gradually heated to 110° C. (>2 hours, 10° C./min.). The impregnated catalyst mixture was then calcined at 500° C. (6 hours, 1° C./min).

EXAMPLE B

Preparation of 5 Weight Percent Cobalt and 0.5 Weight Percent Palladium on Graphite Powdered and meshed graphite (100 g) of uniform particle size distribution of about 0.2 mm was dried at 120° C. in an oven under nitrogen atmosphere overnight and then cooled to room temperature. To this was added a solution of palladium nitrate (Heraeus) (1.1 g) in distilled water (11 ml). The resulting slurry was dried in an oven gradually heated to 110° C. (>2 hours, 10° C./min.). The impregnated catalyst mixture was then calcined at 500° C. (6 hours, 1° C./min). To this calcined and cooled material was added a solution of cobalt nitrate hexahydrate (24.7 g) in distilled water (25 ml). The resulting slurry was dried in an oven gradually heated to 110° C. (>2 hours, 10° C./min.). The impregnated catalyst mixture was then calcined at 500° C. (6 hours, 1° C./min).

EXAMPLE C

Preparation of 10 Weight Percent Cobalt and 1 Weight Percent Platinum on High Purity Silica Powdered and meshed high purity silica (100 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min.). The impregnated catalyst mixture was then calcined at 500° C. (6 hours, 1° C./min.). To this calcined and cooled material was added a solution of cobalt nitrate hexahydrate (49.4 g) in distilled water (50 ml). The resulting slurry was dried in an oven gradually heated to 110° C. (>2 hours, 10° C./min.). The impregnated catalyst mixture was then calcined at 500° C. (6 hours, 1° C./min.).

EXAMPLE D

Preparation of 10 Weight Percent Cobalt and 1 Weight Percent Platinum on Calcium Silicate Powdered and meshed calcium silicate (100 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min.). The impregnated catalyst mixture was then calcined at 500° C. (6 hours, 1° C./min.). To this calcined and cooled material was added a solution of cobalt nitrate hexahydrate (49.4 g) in distilled water (50 ml). The resulting slurry was dried in an oven gradually heated to 110° C. (>2 hours, 10° C./min.). The impregnated catalyst mixture was then calcined at 500° C. (6 hours, 1° C./min.).

EXAMPLE E

Preparation of 10 Weight Percent Cobalt and 1 Weight Percent Chromium on Graphite Powdered and meshed graphite (100 g) of uniform particle size distribution of about 0.2 mm was dried at 120° C. in an oven under nitrogen atmosphere overnight and then cooled to room temperature. To this was added a solution of chromium nitrate nonahydrate (Alfa Aesar) (6.5 g) in distilled water (13 ml). The resulting slurry was dried in an oven gradually heated to 110° C. (>2 hours, 10° C./min.). The impregnated catalyst mixture was then calcined at 500° C. (6 hours, 1° C./min). To this calcined and cooled material was added a solution of cobalt nitrate hexahydrate (49.4 g) in distilled water (50 ml). The resulting slurry was dried in an oven gradually heated to 110° C. (>2 hours, 10° C./min.). The impregnated catalyst mixture was then calcined at 500° C. (6 hours, 1° C./min). Gas Chromatographic (GC) analysis of the Products The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

EXAMPLE 1

The catalyst utilized was 10 weight percent cobalt and 1 weight percent palladium on Graphite prepared in accordance with the procedure of Example A In a tubular reactor made of stainless steel, having an internal diameter of 30 mm and capable of being raised to a controlled temperature, there are arranged 50 ml of 10 weight percent cobalt and 1 weight percent palladium on Graphite. The length of the catalyst bed after charging was approximately about 70 mm.

A feed liquid was comprised essentially of acetic acid. The reaction feed liquid was evaporated and charged to the reactor along with hydrogen and helium as a carrier gas with an average combined gas hourly space velocity (GHSV) of about 2500 $hr^{-1}$ at a temperature of about 250° C. and pressure of 22 bar. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to ethanol was 97.5% at a conversion of acetic acid of 18.5%.

EXAMPLE 2

The catalyst utilized was 5 weight percent cobalt and 0.5 weight percent platinum on graphite prepared in accordance with the procedure of Example B.

The procedure as set forth in Example 1 is substantially repeated with an average combined gas hourly space velocity (GHSV) of 2,500 hr$^{-1}$ of the feed stream of the vaporized acetic acid and hydrogen at a temperature of 225° C. and pressure of 22 bar. A portion of the vapor effluent is passed through a gas chromatograph for analysis of the contents of the effluents. The acetic acid conversion is 20% and ethanol selectivity is 95%.

EXAMPLE 3

The catalyst utilized was 10 weight percent cobalt and 1 weight percent platinum on High Purity Silica prepared in accordance with the procedure of Example C.

The procedure as set forth in Example 1 was substantially repeated with an average combined gas hourly space velocity (GHSV) of 2,500 hr$^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion was 71% and ethanol selectivity was 96%.

EXAMPLE 4

The catalyst utilized was 10 weight percent cobalt and 1 weight percent platinum on calcium silicate prepared in accordance with the procedure of Example D.

The procedure as set forth in Example 1 was substantially repeated with an average combined gas hourly space velocity (GHSV) of 2,500 hr$^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion was 50% and ethanol selectivity was 94%.

EXAMPLE 5

The catalyst utilized was 10 weight percent cobalt and 1 weight percent chromium on graphite prepared in accordance with the procedure of Example E.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion is 38% and ethanol selectivity is 96%.

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A method for producing ethanol from biomass, said method comprising:
   (i) converting said biomass into a first stream comprising syngas;
   (ii) catalytically converting at least some of said syngas into a second stream comprising methanol;
   (iii) separating some of said syngas into hydrogen and carbon monoxide;
   (iv) catalytically converting at least some of said methanol with some of said carbon monoxide into a third stream comprising acetic acid; and
   (v) reducing at least some of said acetic acid with some of said hydrogen into a fourth stream comprising ethanol.

2. The process according to claim 1, wherein step (i) includes hydrogasification of solid and/or liquid carbonaceous materials to obtain a process gas which is steam pyrolized to form the syngas.

3. The process according to claim 1, wherein the reducing occurs in the presence of a catalyst comprising cobalt.

4. The process according to claim 3, wherein the reducing occurs in the presence of a catalyst comprising molybdenum.

5. The process according to claim 1, wherein the reducing occurs in the presence of a catalyst comprising cobalt and a second metal on a catalyst support, wherein the cobalt is present in an amount from 0.1 weight percent to 20 weight percent, and wherein the second metal is selected from the group consisting of palladium, platinum, and chromium.

6. The process according to claim 5, wherein the catalyst support is selected from the group consisting of silica, alumina, calcium silicate, carbon, zirconia and titania.

7. The process according to claim 5, wherein the second metal is palladium.

8. The process according to claim 7, wherein the loading of cobalt is from 4 to 12 weight percent and the loading of palladium is from 0.5 to 2 weight percent and the catalyst support is graphite.

9. The process according to claim 5, wherein the second metal is platinum.

10. The process according to claim 9, wherein cobalt loading is from 4 to 12 weight percent and platinum loading is from 0.5 to 2 weight percent and the catalyst support is high purity silica.

11. The process according to claim 5, wherein selectivity to ethanol based on acetic acid consumed is at least 40 percent.

12. The process according to claim 5, wherein selectivity to ethanol based on acetic acid consumed is at least 60 percent.

13. The process according to claim 5, wherein selectivity to ethanol based on acetic acid consumed is at least 80 percent.

14. The process according to claim 5, wherein selectivity to ethanol based on acetic acid consumed is at least 95 percent.

15. The process according to claim 5, wherein the reducing is carried out at a temperature in the range of 225° to 275° C.

16. The process according to claim 5, wherein the cobalt is present in an amount from 1 weight percent to 15 weight percent.

17. A method for producing ethanol from biomass, said method comprising:
   (i) converting said biomass into syngas;
   (ii) reacting the syngas in the presence of a catalyst to form methanol;
   (iii) supplying part of the syngas to a separator unit to recover carbon monoxide and hydrogen;
   (iv) carbonylating the methanol with the carbon monoxide to form acetic acid; and
   (v) reducing at least some of the acetic acid with the hydrogen to form the ethanol.

18. The process according to claim 17, wherein step (i) includes hydrogasification of solid and/or liquid carbonaceous materials to obtain a process gas which is steam pyrolized to form the syngas.

19. The process according to claim 17, wherein the reducing occurs in the presence of a catalyst comprising cobalt.

20. The process according to claim 19, wherein the reducing occurs in the presence of a catalyst comprising molybdenum.

21. The process according to claim 17, wherein the reducing occurs in the presence of a catalyst comprising cobalt and a second metal on a catalyst support, wherein the cobalt is present in an amount from 0.1 weight percent to 20 weight percent, and wherein the second metal is selected from the group consisting of palladium, platinum, and chromium.

22. The process according to claim 21, wherein the catalyst support is selected from the group consisting of silica, alumina, calcium silicate, carbon, zirconia and titania.

23. The process according to claim 21, wherein the second metal is palladium.

24. The process according to claim 23, wherein the loading of cobalt is from 4 to 12 weight percent and the loading of palladium is from 0.5 to 2 weight percent and the catalyst support is graphite.

25. The process according to claim 21, wherein the second metal is platinum.

26. The process according to claim 25, wherein cobalt loading is from 4 to 12 weight percent and platinum loading is from 0.5 to 2 weight percent and the catalyst support is high purity silica.

27. The process according to claim 21, wherein selectivity to ethanol based on acetic acid consumed is at least 40 percent.

28. The process according to claim 21, wherein selectivity to ethanol based on acetic acid consumed is at least 60 percent.

29. The process according to claim 21, wherein selectivity to ethanol based on acetic acid consumed is at least 80 percent.

30. The process according to claim 21, wherein selectivity to ethanol based on acetic acid consumed is at least 95 percent.

31. The process according to claim 21, wherein the reducing is carried out at a temperature in the range of 225° to 275° C.

32. The process according to claim 21, wherein the cobalt is present in an amount from 1 weight percent to 15 weight percent.

* * * * *